US00PP09106P

United States Patent [19]

Jacobsen

[11] Patent Number: Plant 9,106

[45] Date of Patent: Apr. 11, 1995

[54] POINSETTIA PLANT 'PJ 3219'

[75] Inventor: Peter Jacobsen, Skibby, Denmark

[73] Assignee: Paul Ecke Ranch, Encinitas, Calif.

[21] Appl. No.: 192,720

[22] Filed: Feb. 7, 1994

[51] Int. Cl.[6] ..... A01H 5/00

[52] U.S. Cl. ..... Plt./86.4

[58] Field of Search ..... Plt. 86.4

[56] References Cited

PUBLICATIONS

Sigurbjörnsson, B., "Chapter 8 Induced Mutations" *Crop Breeding* 1983 American Society of Agronomy and Crop Science Society of America, pp. 153–176.

*Primary Examiner*—James R. Feyrer

*Attorney, Agent, or Firm*—Arnold, White & Durkee

[57] ABSTRACT

Poinsettia 'PJ 3219' is a new cultivar, distinguished by smooth red bracts, large flowers, strong stems and self-branching characteristics. 'PH 3219' is a sport of the red bracted 'Supjibi' (U.S. Plant Pat. No. 6592) with the same flowering response and cultural requirements. The new plant produces a very desirable branched flowering pot plant. The new plant is resistant to epinasty after being confined to shipping containers and recovers rapidly if the plant does become epinastic. The post-production foliage and bract retention is good.

1 Drawing Sheet

BACKGROUND OF THE NEW PLANT

This new poinsettia cultivar originated as an induced smooth bracked sport of 'Supjibi' (U.S. Plant Pat. No. 6,592) in my greenhouse in Skibby, Denmark. It was induced through irradiation of vegetative plants with 2500 rads of gamma radiation, randomly applied to the whole plant. A single plant from the irradiated group exhibited smooth orange-red bracts. The mutant was characterized by it strong stems, large flowers, self branching, smooth orange-red bracts and large green leaves, traits which help distinguish it from other poinsettia cultivars, and seem to make it a desirable plant for commercial greenhouse production. No other similar plants were observed from the irradiation nor were any other changes in the plant observed which would appear to have commercial merit. 'PJ 3219' differed from its parent 'Supjibi' in having smoother bracts as compared to the puckered bracts of 'Supjibi'. The leaves and bracts of 'PJ 3219' are relatively narrower than those of 'Supjibi', and the bract petioles somewhat longer. The red bract color is not as orange as 'Supjibi', with 'PJ 3219' having more blue tones.

Tip cuttings were taken from the mature mutant plant and propagated under controlled greenhouse conditions in Encinitas, Calif. At least 3–5 generations of cuttings were made from the mutant plant. The characteristics of PJ3219 held true from generation to generation.

DESCRIPTION OF THE PHOTOGRAPHS

Poinsettia 'PJ 3219' is illustrated in the accompanying color photographs.

The upper photo is a side view of 3 single stem plants per pot in full flower.

The lower photo is a top view of the same plants showing flower and bract formation.

DESCRIPTION OF THE PLANT

The following is a detailed description of this new poinsettia as observed in Encinitas, Calif., U.S.A. during December 1992. Observations were recorded from flowering plants, grown as 3 single stem plants per pot. The pot was 14 cm. in diameter and 11 cm. in height. Color designations are compared to the 1986 edition of R.H.S. Colour Chart, first published in 1966 by the Royal Horticultural Society, London, England.

THE PLANT

Origin: Sport of 'Supjibi' (U.S. Plant Pat. No. 6,592), induced through irradiation of vegetative plants with 2500 rads of gamma radiation.

Classification:

*Botanic.*—*Euphorbia pulcherrima* Willd.

*Common name.*—Poinsettia.

*Cultivar name.*—'PJ 3219'.

Form: Shrub.

Height: Short.

Growth habit: As a single stemmed plant, upright and vigorous with self-branching side shoots. The application of a chemical growth retardant may be needed to restrict height for commercial pot plant production. I observed 3 unpinched plants in a pot with an overall height of 39 cm. and an overall width of 53 cm. The bract diameter of individual flowers was 33 cm.

Branching: Axillary branches will develop and terminate in a flower without pinching. However, it is usually desirable to pinch 'PJ 3219' before flower induction and remove all terminal dominance. Then, all axillary branches will develop uniformly and at a faster rate.

Growth rate: Rooting of stem cutting occurs in 12–18 days under intermittent mist.

Flowering: The plant will flower in eight to nine weeks under continuous long night conditions and night temperatures of about 16–18 degrees C. Like its parent, ('Supjibi'), 'PJ 3219' will be in full bloom in late November in the northern hemisphere under natural daylength conditions.

Foliage: At flowering, plants were observed with about 14 uniformity dark green leaves, one leaf per node. The leaves were of medium size, leaf blades typically being 14–15 cm. long and 10–11 cm. wide with leaf petioles 6–7 cm. long. Between the green leaves and the true flower bracts were 6 transitional bracts from the uppermost nodes on each stem. These leaf/bracts were green but changed to red as the flowers matured. At maturity, one to two of these leaf/bracts were neither completely green nor completely red.

*Leaf shape.*—Typical leaves are generally ovate with obtuse bases and acuminate tips. Leaf margins are mostly entire with 1 or 2 indentations on each side of the lower-most leaves.

*Color.*—Upper side — Green, slightly darker than RHS 147A. Under side — Green, a little darker than RHS 147B.

Bracts: Generally there were 18–21 red bracts of various sizes subtending the cyathia. The primary bracts are large, have blades typically 15–17 cm. long and 11–12 cm. wide with petioles 4–5 cm. long.

*Shape.*—Primary bracts are ovate with acute bases and acuminate tips. Leaf margins are entire or weakly lobed with 1 small indentation on either side of the bract. Secondary bracts are ovate to elliptic and have entire margins.

*Color.*—Upper side — Orange-red. RHS 45A-B. Under side — Light red. RHS 45C-D.

Flowers: Generally, 19–22 cyathia (flowers) were present when the plant was in full bloom. Each cyathium is about 7–8 mm long and 7–8 mm wide, green in color, and fringed with red at the distal ends. Usually one, but occasionally two yellow nectar cups protrude from the side of each cyathium. The flower pedicel is also green and about 5 mm in length. The stamens protruding from the cyathia are red. The anthers are bifurcate with copious yellow pollen. The stigmas are dark red and trifurcate. Cyathia retention was about three weeks beyond the time the flower was fully mature.

*Nectar exudate.*—Present, abundant.

*Seed formation.*—Self-incompatible.

*Fertility.*—Not observed.

Post production: 'PJ 3219' is resistant to epinasty after being confined to shipping containers and recovers rapidly if the plant does become epinastic. The foliage and bract retention is good.

What is claimed is:

1. A new and distinct Poinsettia cultivar, substantially as herein shown and described, distinguished by its strong stems, smooth red bracts, self branching, large flowers and good leaf and bract retention in the consumer environment.

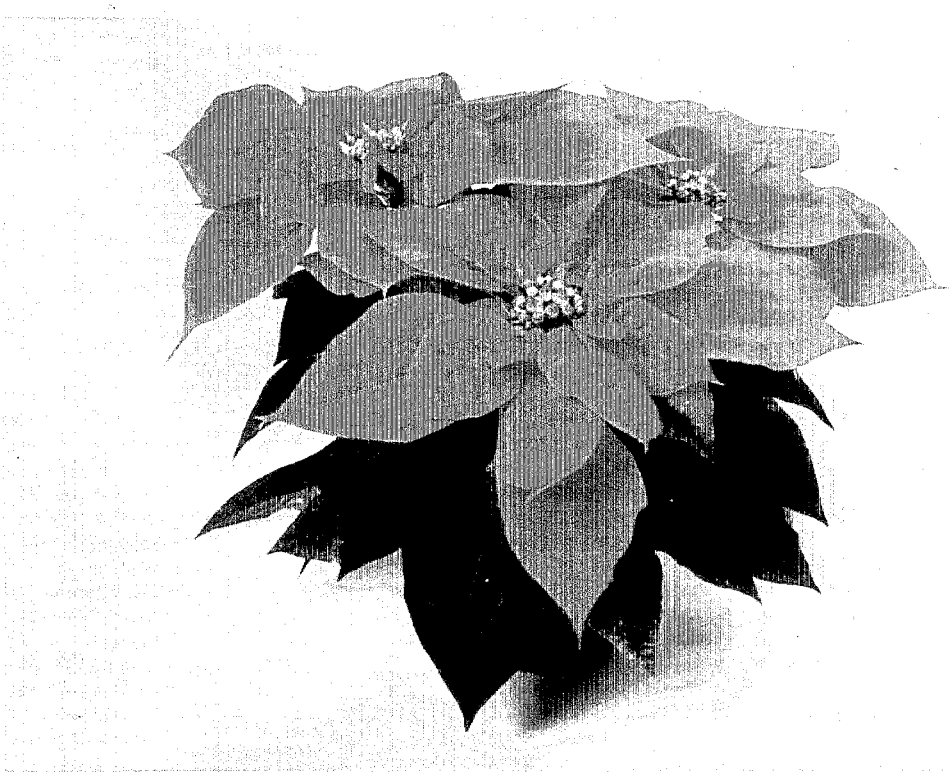
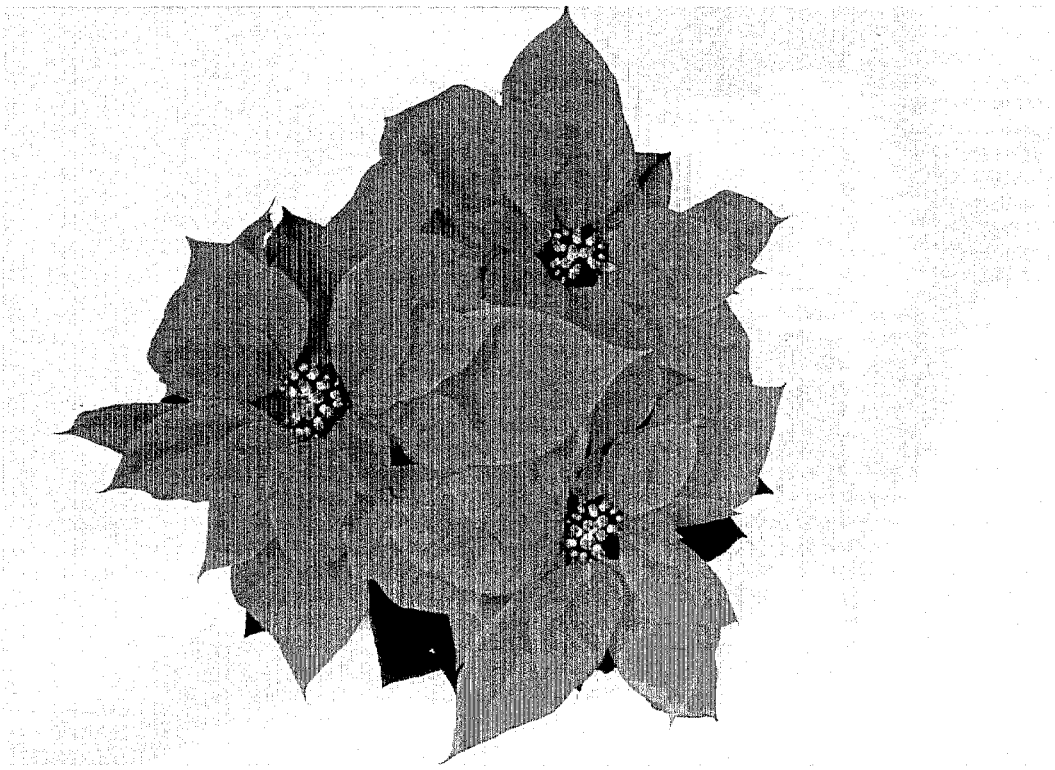

* * * * *